United States Patent [19]

Vacanti et al.

[11] Patent Number: 5,716,404
[45] Date of Patent: Feb. 10, 1998

[54] BREAST TISSUE ENGINEERING

[75] Inventors: Joseph P. Vacanti, Winchester; Anthony Atala, Weston, both of Mass.; David J. Mooney, Ann Arbor, Mich.; Robert S. Langer, Newton, Mass.

[73] Assignee: Massachusetts Institute of Technology, Cambridge, Mass.

[21] Appl. No.: 358,189

[22] Filed: Dec. 16, 1994

[51] Int. Cl.$^6$ .................................................. A61F 2/12
[52] U.S. Cl. .................................................. 623/8; 128/898
[58] Field of Search ...................... 623/8, 11, 12, 623/66; 435/178, 173, 240, 241, 32; 424/240.1, 240.23; 128/898

[56] References Cited

U.S. PATENT DOCUMENTS

| | | | |
|---|---|---|---|
| 1,995,970 | 3/1935 | Dorough | 260/2 |
| 2,609,347 | 9/1952 | Wilson | 260/2.5 |
| 2,653,917 | 9/1953 | Hammon | 260/2.5 |
| 2,659,935 | 11/1953 | Hammon | 18/55 |
| 2,664,366 | 12/1953 | Wilson | 117/138.8 |

(List continued on next page.)

FOREIGN PATENT DOCUMENTS

| | | |
|---|---|---|
| B-24245/88 | 2/1989 | Australia . |
| 0 153 896 | 9/1985 | European Pat. Off. . |
| 0 248 246 | 6/1986 | European Pat. Off. . |
| 0 248 247 | 6/1986 | European Pat. Off. . |
| 0 226 061 | 6/1987 | European Pat. Off. . |
| 0 282 746 | 9/1988 | European Pat. Off. . |
| 0 339 607 | 11/1989 | European Pat. Off. . |

(List continued on next page.)

OTHER PUBLICATIONS

Anderson, Kathryn D., "Gene Expression in Implanted Rat Hepatocytes Following Retroviral–Mediated Gene Transfer," Somatic Cell & Mol. Gen., 15(3):215–227 (1989).

Anderson, David J., Caltech Bioloqy, 1987.

Alberts, Bruce, et al. Molecular Biology of The Cell Garland Publishing, Inc., pp. 893–894.

Atala & Casale, "Management of Primary Vesicoureteral Reflux," Infections in Urology pp. 39–43 (Mar./Apr., 1990).

(List continued on next page.)

*Primary Examiner*—David Isabella
*Attorney, Agent, or Firm*—Arnall Golden & Gregory, LLP

[57] ABSTRACT

Methods and compositions are described herein for reconstruction or augmentation of breast tissue. Dissociated cells, preferably muscle cells, are implanted in combination with a suitable biodegradable, polymeric matrix to form new tissue. There are two forms of matrices which can be used: a polymeric hydrogel formed of a material such as alginate having cells suspended therein, and a fibrous matrix having an interstitial spacing between about 100 and 300 microns. Preferred polymeric materials are those degrading over about one to two months, such as polylactic acid-glycolic acid copolymers. The matrices can be seeded prior to implantation or implanted, allowed to vascularize, then seeded with cells. In a preferred embodiment, the cell-matrix structures are implanted in combination with tissue expander devices. As cell-matrix is implanted, or cells proliferate and form new tissue, the expander size is decreased, until it can be removed and the desired reconstruction or augmentation is obtained. The preferred cell types are muscle cells, although other types of mesenchymal cells, fibroblasts, chondrocytes, and adipocytes can be used. Cells obtained from tissue such as the labia can be used for specialized applications such as formation of a nipple type tissue. Other materials, such as bioactive molecules that enhance vascularization of the implanted tissue and/or which inhibit ingrowth of fibrotic tissue, can be implanted with the matrix to enhance development of more normal tissue.

11 Claims, 3 Drawing Sheets

U.S. PATENT DOCUMENTS

| | | | |
|---|---|---|---|
| 2,676,945 | 4/1954 | Higgins | 260/45.7 |
| 2,683,136 | 7/1954 | Trehu | 260/78.3 |
| 2,703,316 | 3/1955 | Schneider | 260/78.3 |
| 2,846,407 | 8/1958 | Wilson | 260/2.5 |
| 2,951,828 | 9/1960 | Zeile | 260/77.5 |
| 3,531,561 | 9/1970 | Trehu | 264/210 |
| 3,826,241 | 7/1974 | Bucalo | 128/1 R |
| 3,880,991 | 4/1975 | Yolles | 424/22 |
| 3,883,393 | 5/1975 | Knazek et al. | 195/1.8 |
| 3,902,497 | 9/1975 | Casey | 128/296 |
| 3,935,065 | 1/1976 | Doerig | 195/1.7 |
| 3,949,073 | 4/1976 | Daniels et al. | 424/177 |
| 3,960,150 | 6/1976 | Hussain et al. | 128/260 |
| 3,974,526 | 8/1976 | Dardik et al. | 3/1.4 |
| 3,992,725 | 11/1976 | Homsy | 3/1 |
| 3,995,444 | 12/1976 | Clark et al. | 62/306 |
| 4,026,304 | 5/1977 | Levy | 128/419 |
| 4,060,081 | 11/1977 | Yannas et al. | 128/156 |
| 4,069,307 | 1/1978 | Higuchi et al. | 424/22 |
| 4,137,921 | 2/1979 | Okuzumi | 128/335.5 |
| 4,141,087 | 2/1979 | Shalaby et al. | 3/1 |
| 4,144,126 | 3/1979 | Burbidge | 195/1.1 |
| 4,186,448 | 2/1980 | Brekke | 3/1.9 |
| 4,192,827 | 3/1980 | Mueller et al. | 525/123 |
| 4,205,399 | 6/1980 | Shalaby et al. | 3/1 |
| 4,228,243 | 10/1980 | Iizuka | 435/285 |
| 4,239,664 | 12/1980 | Teag et al. | 260/17.4 |
| 4,243,775 | 1/1981 | Rosensaft et al. | 525/415 |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 435/240 |
| 4,328,204 | 5/1982 | Wasserman et al. | 424/19 |
| 4,347,847 | 9/1982 | Usher | 128/334 |
| 4,348,329 | 9/1982 | Chapman | 260/403 |
| 4,352,883 | 10/1982 | Lim | 435/178 |
| 4,356,261 | 10/1982 | Kuettner | 435/68 |
| 4,391,797 | 7/1983 | Folkman et al. | 424/19 |
| 4,416,986 | 11/1983 | Markus et al. | 435/68 |
| 4,427,808 | 1/1984 | Stol et al. | 524/24 |
| 4,431,428 | 2/1984 | Schmer | 604/897 |
| 4,438,198 | 3/1984 | Schmer | 435/178 |
| 4,439,152 | 3/1984 | Small | 433/173 |
| 4,440,921 | 4/1984 | Allcock | 528/168 |
| 4,444,887 | 4/1984 | Hoffmann | 435/240 |
| 4,446,229 | 5/1984 | Indech | 435/1 |
| 4,446,234 | 5/1984 | Russo et al. | 435/29 |
| 4,450,150 | 5/1984 | Sidman | 424/1.1 |
| 4,456,687 | 6/1984 | Green | 435/241 |
| 4,458,678 | 7/1984 | Yannas et al. | 128/155 |
| 4,485,096 | 11/1984 | Bell | 623/15 |
| 4,485,097 | 11/1984 | Bell | 424/95 |
| 4,489,056 | 12/1984 | Himmelstein et al. | 424/22 |
| 4,494,385 | 1/1985 | Kuraoka et al. | 62/306 |
| 4,495,174 | 1/1985 | Allcock | 424/78 |
| 4,501,815 | 2/1985 | Reid et al. | 623/66 |
| 4,505,266 | 3/1985 | Yannas et al. | 623/15 |
| 4,520,821 | 6/1985 | Schmidt et al. | 128/334 |
| 4,528,265 | 7/1985 | Becker | 435/172.1 |
| 4,544,516 | 10/1985 | Hughes et al. | 264/108 |
| 4,545,082 | 10/1985 | Hood | 623/1 |
| 4,553,272 | 11/1985 | Mears | 623/1 |
| 4,559,298 | 12/1985 | Fahy | 435/1 |
| 4,559,304 | 12/1985 | Kasai et al. | 435/240 |
| 4,563,350 | 1/1986 | Nathan et al. | 424/95 |
| 4,563,490 | 1/1986 | Stol et al. | 524/24 |
| 4,576,608 | 3/1986 | Homsy | 623/11 |
| 4,595,713 | 6/1986 | St. John | 523/105 |
| 4,609,551 | 9/1986 | Caplan et al. | 623/66 |
| 4,627,853 | 12/1986 | Campbell et al. | 623/16 |
| 4,637,931 | 1/1987 | Schmitz | 424/73 |
| 4,642,120 | 2/1987 | Nevo et al. | 623/11 |
| 4,645,669 | 2/1987 | Reid | 424/95 |
| 4,675,189 | 6/1987 | Kent et al. | 424/490 |
| 4,675,284 | 6/1987 | Leevy et al. | 435/6 |
| 4,681,763 | 7/1987 | Nathanson et al. | 424/95 |
| 4,689,293 | 8/1987 | Goosen et al. | 435/1 |
| 4,713,070 | 12/1987 | Mano | 623/1 |
| 4,721,096 | 1/1988 | Naughton et al. | 128/1 |
| 4,734,373 | 3/1988 | Bartal | 435/296 |
| 4,757,017 | 7/1988 | Cheung | 435/240.23 |
| 4,757,128 | 7/1988 | Domb et al. | 528/271 |
| 4,778,749 | 10/1988 | Vasington et al. | 435/2 |
| 4,846,835 | 7/1989 | Grande | 623/11 |
| 4,853,324 | 8/1989 | Viles et al. | 435/2 |
| 4,868,121 | 9/1989 | Scharp et al. | 435/268 |
| 4,880,622 | 11/1989 | Allcock et al. | 424/78 |
| 4,891,225 | 1/1990 | Langer et al. | 424/428 |
| 4,946,938 | 8/1990 | Magill et al. | 528/399 |
| 4,963,489 | 10/1990 | Naughton et al. | 435/240.1 |
| 4,988,761 | 1/1991 | Ikada et al. | 524/557 |
| 5,000,963 | 3/1991 | Hefton | 623/15 |
| 5,032,508 | 7/1991 | Naughton et al. | 435/32 |
| 5,041,138 | 8/1991 | Vacanti et al. | 623/16 |
| 5,326,357 | 7/1994 | Kandel | 623/11 |
| 5,512,475 | 4/1996 | Naughton et al. | 623/11 |

FOREIGN PATENT DOCUMENTS

| | | |
|---|---|---|
| 28 53 614 | 7/1979 | Germany. |
| 35 18 150 | 10/1986 | Germany. |
| 0 153 895 | 9/1985 | Japan. |
| 62 011 459 | 1/1987 | Japan. |
| 63 074 498 | 4/1988 | Japan. |
| 63 196 273 | 8/1988 | Japan. |
| 63 196 595 | 8/1988 | Japan. |
| WO 87/06120 | 10/1987 | WIPO. |
| WO 88/03785 | 6/1988 | WIPO. |
| WO 89/00413 | 1/1989 | WIPO. |
| WO 89/07944 | 9/1989 | WIPO. |
| WO 90/12603 | 11/1990 | WIPO. |
| WO 90/12604 | 11/1990 | WIPO. |
| WO 92/07525 | 5/1992 | WIPO. |
| WO 93/07913 | 4/1993 | WIPO. |
| WO 93/08850 | 5/1993 | WIPO. |
| WO 94/21299 | 9/1994 | WIPO. |
| WO 94/25079 | 11/1994 | WIPO. |

OTHER PUBLICATIONS

Atala, A., et al., "Endoscopic Treatment of Vesicoureteral Reflux with a Chondrocyte–Alginate Suspension," The Journal of Urology 152:641–643 (Aug., 1994).

Atala, A., et al., "Endoscopic Treatment of Vesicoureteral Reflux with a Self–Detachable Balloon System," The Journal of Urology 148:724–728 (Aug., 1992).

Atala, A., et al. "Injectable Alginate Seeded with Chondrocytes as a Potential Treatment for Vesicoureteral Reflux," The Journal of Urology 150:745–747 (Aug., 1993).

Atala, A., et al., "Laparoscopic Correction of Vesicoureteral Reflux," The Journal of Urology 150:748–751 (Aug., 1993).

Atala, A., et al., "Sonography with Sonicated Albumin in the Detection of Vesidoureteral Reflux," The Journal of Urology 150:756–758 (Aug., 1993).

Baklund, Erik–olof, et al. "Toward a Transplantation Therapy in Parkinson's Disease," Annals of the N.Y. Acad. of Sci. 495:658–673 (1987).

Bazeed, Mahmoud, et al. "New Surgical Procedure for Management of Peyronie Disease," Urology 21(5), 501–504 (1983).

Ben-Ze'ev, Avri, et al. "Cell–Cell and Cell–Matrix Interactions Differentially Regulate the Expression of Hepatic and Cytoskeletal Genes in Primary Cultures of Rat Hepatocytes," Proc. Natl. Acad. Sci. USA 85:2161–2165 (Apr. 1988).

Berrino, Pietro, et al. "Surgical Correction of Breast Deformities Following Long–Lasting Complications of Polyurethane–Covered Implants," Ann. Plast. Surg., 24:481 (1990).

Biers, Elizabeth. "Organogenesis' Human Artery Equivalent May Revolutionize Vascular Grafts," Genetic Engineering News (Nov./Dec. 1987).

Bissell, D. Montgomery, et al., "Interactions of Rat Hepatocytes with Type IV Collagen, Fibronectin and Laminin Matrices, Distinct Matrix–Controlled Modes of Attachment and Spreading," European Journ. of Cell Biology 40:72–78 (1986).

Bissell, D. M., et al. "The Role of Extracellular Matrix in Normal Liver," Scand. J. Gastroenterol., 23:107 (1988).

Bissell, D. Montgomery, "Support of Cultured Hepatocytes by a Laminin–Rich Gel," J. Clin. Invest. 79:801–812 (1987).

Bjorklund, Annals of the N.Y. Academy of Science 495:676–686 (1987).

Blaivas, Jerry, et al., "When Sphincter Failure is the Cause of Female Stress Incontinence," Contemporary Urology 5(3):33–54 (Mar., 1993).

Bohn, Martha C., et al., "Adrenal Medulla Grafts Enhance Recovery of Striatal Dopaminergic Fibers," Science 238(4817):913–916 (Aug. 21, 1987).

"Brain Graft Seeks to Relieve Huntington Disease Patient," New York Times (Mar. 4, 1988).

Brown, Norman, "Fibrin–Collagen Nerve Repair Device," Inventors: Russ Griffiths, Larry Stensaas & Ken Horch, Letter dated May 10, 1988.

Burke, "The Effects of the Configuration of an Artificial Extracellular Matrix on the Development of a Functional Dermis," The Role of Extracellular Matrix in Development 351–355 (Alan R. Liss, Inc., NY 1984).

Cao, Y., et al., "The Generation of Neo–Tendon Using Synthetic Polymers seeded with Tenocytes," Transplantation Proceedings, 26(6):3390–3392 (1994).

Chaikin, Andrew, "Tissue Engineering: Science Non–Fiction," Medical Industry Executive pp. 6–7 (May, 1993).

Chuang, Vincent P., et al. "Sheath Needle for Liver Biopsy in High–Risk Patients," RSNA pp. 261–262 (1988).

Cilento, Bartley, et al., "Phenotypic and Cytogenetic Characterization of Human Bladder Urothelia Expanded in Vitro," Microbiology & Immunology 152:665–670 (Aug., 1994).

Claes, H., et al., "Pulmonary Migration Following Periurethral Polytetrafluorethylene Injection for Urinary Incontinence," The Journal of Urology 142:821–822 (Sep. 1989).

Cosimi, et al. "Transplantation of Skin," Surgical Clinics of N.A. 585(2), 435–451 (Apr., 1978).

Collier, T. J. et al., "Norepinephrine Deficiency and Behavioral Senescence in Aged Rats: Transplanted Locus Ceruleus Neurons as an Experimental Replacement Therapy," Annals of the New York Academy of Science 495:396–403 (1987).

Culliton, Barbara J., "Gore Tex Organoids and Genetic Drugs," Science 246:747–749 (1989).

da Silva, C. F., "An In Vivo Model to Quantify Motor and Sensory Peripheral Nerve Regeneration Using Bioresorbable Nerve Guide Tubes," Brain Research, 342:307–315 (1985).

Davis, George E., et al., "Human Amnion Membrane Serves as a Substratum for Growing Axons in Vitro and in Vivo," Science, 236:1106–1109 (May 29, 1987).

del Cerro, M., et al., "Retinal Transplants into One Anterior Chamber of the Rat Eye," Neuroscience 21:(3)707–23 (Jun. 1987).

Doillon, C. J., et al., "Collagen–Based Wound Dressings: Control of the Pore Structure and Morphology," Journal of Biomedical Materials Research, 20:1219–1228 (1986).

Doillon, C. J. et al., "Epidermal Cells Cultured on a Collagen–Based Material," G. W. Bailey, Editor, Proceedings of the 44th Annual Meeting of the Electron Microscopy Society of America, (1986).

Ebata, et al. "Liver Regeneration Utilizing Isolated Hepatocytes Transplanted into the Rat Spleen," Surg. Forum 29:338–340 (1978).

Elkowitz, A., et al., "Various Methods of Breast Reconstruction After Mastectomy: An Economic Comparison," Plastic and Reconstructive Surgery, 92(1):77–83 (Jul. 1993).

Erickson, Deborah, "Material Help," Scientific American pp. 114–116 (Aug., 1992).

Ferro, M. A., et al., "Periurethral Granuloma: Unusual Complication of Teflon Periurethral Injection," Urology 31(5):422–423 (May, 1988).

Folkman, Judah, et al., "Angiogenic Factors," Science 235:442–447 (Jan. 23, 1987).

Fontaine, H., et al., "Optimization Studies on Retroviral Mediated Gene Transfer into Rat Hepatocytes: Implications for Gene Therapy," The Society of University Surgeons, Resident's Program, Cincinnati, Ohio Feb. 15, 1992).

Freshney, "The Culture Environment: I. Substrate, Gas Phase, and Temperature," Culture of Animal Cells pp. 55–56 (Alan R. Liss, NY 1983).

Gash, D. M., et al., "Amitotic Neuroblastoma Cells Used for Neural Implants in Monkeys," Science 233(4771):1420–2 (Sep. 26, 1986).

Gash, D. M. "Neural Transplantation: Potential Therapy for Alzheimer's Disease," J. Neural Trans. [Suppl] 24:301–8 (1987).

Geiss, S., et al., "Multicenter Survey of Endoscopic Treatment of Vesidoureteral Reflux in Children," Eur. Urol 17:328–329 (1990).

Gilbert, James C., et al., "Cell Transplantation of Genetically Altered Cells on Biodegradable Polymer Scaffolds in Syngeneic Rats," Department of Surgery, The Children's Hospital and Harvard Medical School, Boston, Massachusetts.

Grande, Daniel A., et al., "Healing of Experimentally Produced Lesions in Articular Cartilage Following Chondrocyte Transplantation," The Anatomical Record 218:142–148 (1987).

Grande, Daniel A., et al., "The Repair of Experimentally Produced Defects in Rabbit Articular Cartilage by Autologous Chondrocyte Transplantations," (May 11, 1988).

Green, Howard, "Growth of Cultured Human Epidermal Cells into Multiple Epithelia Suitable for Grafting," Proc. Natl. Acad. Sci. USA 76(11):5665–5668 (Nov., 1979).

Groth, C. G., et al., "Correction of Hyperbilirubinemia in the Glucoronyltransferase–Deficient Rat by Intraportal Hepatocyte Transplantation," Transplant. Proc. 9:313–316 (1977).

Harris, A. K., et al. "Silicone Rubber Substrata: A New Wrinkle in the Study of Cell Locomotion," Science 208:177–179 (1980).

Hendren & Atala. "Use of Bowel for Vaginal Reconstruction," The Journal of Urology 152:752–755 (Aug., 1994).

Henly, D. R., et al., "Particulate Silicone for Use in Periurethral Injections: A Study of Local Tissue Effects and a Search for Migration," The Journal of Urology 147(4):376A (Apr., 1992).

Henry, E. W., et al., "Nerve Regeneration Through Biodegradable Polyester Tubes," Exp. Neurol. 90(3): 652–676 (Dec., 1985).

Ingber, D. E., et al., "Cells as Tensecrity Structures: Architectural Regulation of Histodifferentiation by Physical Forces Transduced Over Basement Membrane," Gene Expression During Normal and Malignant Differentiation, L. C. Anderson, et al., editors, pp. 13–32 (Academic Press, Orlando, FL 1985).

Ingber, Donald E., et al., "Endothelial Growth Factors and Extracellular Matrix Regulate DNA Synthesis through Modulation of Cell and Nuclear Expansion," In Vitro Cellular and Developmental Biology 23(5):387–394 May, 1987).

Ingber, et al., "Control of Capillary Morphogenesis: A Molecular System of Mechanical Switches," J. Cell Biol. 107:797a (1988).

Ingber, D. E., "How Does Extracellular Matrix Control Capillary Morphogenesis?" Cell 58:803–805 Sep. 8, 1989).

Ingber, "Growth Control Through Fibronectin–Dependent Modulation of Cell Shaper",: J. Cell Biol. 105:219a (1987).

Ingber, D. E., et al., "Mechanochemical Switching Between Growth Factor–Stimulated Angiogenesis In Vitro: Role of Extracellular Matrix," J. Cell. Biol., 109:317–330 (1989).

Jacksic, et al., "The Use of 'Artificial Skin' for Burns," Ann. Rev. Med. 38:107–116 (1987).

Jauregui, H. O. et al., "Attachment and Long Term Survival of Adult Rat Hepatocytes in Primary Monolayer Cultures: Comparison of Different Substrata and Tissue Culture Medial Formulations," In Vitro Cellular & Development Biology 22(1):13–22 (Jan. 1986).

Jones, Peter A., "Degradation of Artificial Tissue Substrates," Cancer Invasion and Metastasis: Biologic and Therapeutic Aspects, 177–185 (Raven Press, NY 1984).

Klagsbrun, Michael, "Large–Scale Preparation of Chondrocytes," *Methods in Enzymology* vol. LVIII, Academic Press, New York, 1979.

Kleinman, H. K., et al., "Use of Extracellular Matrix Components and Cell Culture," Analytical Biochemistry 166:1–13 (1987).

Klompmaker, J., et al, "Porous Polymer Implants for Repair of Full–Thickness Defects of Articular Cartilage: An Experimental Study in Rabbit and Dog" Biomaterials 13(9):625–634 (1992).

Kolata, Gina, "Parkinson Procedure: Fervor Turns to Disillusion," The New York Times, (Apr. 21, 1988).

Kordower, J. H, et al., "An In Vivo and In Vitro Assessment of Differentiated Neuroblastoma Cells as a source of Donor Tissue for Transplantation," Annals of The New York Academy of Sciences, 495:606–622 (new York 1987).

Kordower, J. H., et al., "Neuroblastoma Cells in Neural Transplants: A Neuroanatomical and Behavioral Analysis," Brain Research, 417:85–98 (1987).

Kretschmer, et al, "Autotransplantation of Pancreatic Fragments to the Portal Vein and Spleen of Total Pancreatectomized Dogs," Ann. Surg., 187:79–86 (Jan., 1978).

Kusano, et al., Acta Japoni Hepato 63:345–351 (1989).

Langer & Moses, "Biocompatible Controlled Release Polymers for Delivery of Polypeptides and Growth Factors," Journal of Cellular Biochemistry, 45:340–345 (1991).

Langer and Vacanti, "Tissue Engineering," Science 260:920–926 (May 14, 1993).

Leonard, M. P., et al., "Endoscopic Injection of Glutaraldehyde Cross–Linked Bovine Dermal Collagen for Correction of Vesidoureteral Reflux," The Journal of Urology 145:115–119 (Jan., 1991).

Leong, K. W., et al., "Bioerodible Polyanhydrides as Drug––Carrier Matrices. I: Characterization, Degradation, and Release Characteristics," Journal of Biomedical Materials Research, 19:941–955 (1985).

Letourneau, Paul C., "Possible Roles of Cell–to–Sutstratus Adhesion in Neuronal Morphogenesis," Developmental Biology, 44:77–91 (1975).

Lewin, "Cloud Over Parkinson's Therapy," Science News, 240:390–392 (1988).

Lewin, "Disappointing Brain Graft Results," Science, p. 1407 (Jun. 10, 1988).

Li, M. L., et al., "Influence of a Reconstituted Basement Membrane and its Components of Casein Gene Expression and Secretion in Mouse Mammary Epithelial Cells",: Proc. Natl. Acad. Sci. USA, 84:136–140 (1987).

Lucas, P., et al, "Ectopic Induction of Cartilage and Bone by Water–Soluble Proteins from Bovine Bone Using a Ppolyanhydride Delivery Vehicle," Journal of Biomedical Materials Research 24(7):901–911 (1990).

Macklis, J. D., et al., "Cross–Linked Collagen Surface for Cell Culture that is Stable, Uniform, and Optically Superior to Conventional Surfaces," In Vitro Cellular & Developmental Biology, 21(3)(1): 189–194 Mar. 1985).

Madison, R. et al., "Increased Rate of Peripheral Nerve Regeneration Using Bioresorbable Nerve Guides and Lamin–Containing Gel," Exp. Neurol., 88(3) 767–772 (Jun. 1985).

Madison, R., et al., "Nontoxic Nerve Guide Tubes Support Neovascular Growth in Transected Rat Optic Nerve," Exp. Neurol. 86:448–461 (1984).

Madison, R., et al., "Peripheral Nerve Regeneration with Entubulation Repair: Comparison of Biodegradeable Nerve Guides Versus Polyethylene Tubes and the Effects of a Laminin–Containing Gel," Exp. Neurol. 95(2)387–390 (Feb., 1987).

Malizia, A., et al., "Migration and Granulomatous Reaction After Periurethral Injection of Polytef (Teflon)" JAMA. 251(24):3277–3281 (Jun., 1984).

Marciano and Gash, "Structural and Functional Relationships of Grafted Vasopressin Neurons," Brain Res., 370(2):338–342 (Apr. 9, 1986).

Matas, et al., "Hepatocellular Transplantation for Metabolic Deficiencies: Decrease of Plasma Bilirubin in Gunn Rats," Science 192:892–894 (1976).

Matouschek, E., "Die Behandlung des vesikorenalen Refluxes durth Transurethrale Einspritzung von Teflonpaste," Urologe A 20:263–264 (1981).

Mesnil, M., et al., "Cell Contact but Not Junctional Communication (Dye Coupling) with Biliary Epithelial Cells is Required for Hepatocytes to Maintain Differentiated Functions," Exper. Cell. Res. 173:524–533 (1987).

Michalopoulos & Pitot, "Primary Culture of Parenchymal Liver Cells on Collagen Membranes," Exper. Cell. Res. 94:70–78 (1975).

Millaruelo, A. L, "Role of Plasminogen Activator and its Inhibitors in Axonal Outgrowth and Regeneration In Vivo," Caltech Biology, (1987).

Minato, et al., "Transplantation of Hepatocytes for Treatment of Surgically Induced Acute Hepatic Failure in the Rat," Eur. Surg. Res., 16:162–169 (1984).

Mittleman & Marraccini, "Pulmonary Teflon Granulomas Following Periurethral Teflon Injection for Urinary Incontinence," Arch. Pathol. Lab. Med. 107:611–612 (Nov. 1983).

Mito, et al., "Hepatocellular Transplantation," Department of Surgery, Asahikawa Medical College 078 4–5 Nishi-Kagura, Asahikawa, Japan.

Mooney, D., "Control of Hepatocyte Function Through Polymer–Substrate Modulation," Thesis Proposal—Department of Chemical Enineering, Massachusetts Institute of Technology (Sep. 22, 1989).

Mooney, D., "Switching from Differentiation to Growth in Hepatocytes: Control by Extracellular Matrix," J. Cell. Phys. (151 ):497–505 (1992).

Mounzer, A. M., et al., "Polyglycolic Acid Mesh in Repair of Renal Injury," Urology 28(2):172–130 (1986).

Movitz, David, "Accessory Spleens and Experimental Splenosis Principles of Growth," The Chicago Medical School Quarterly, 26(4):183–187 (Winter–Spring 1967).

Nail, et al., "Successful Islet Transplantation in Spontaneous Diabetes," Surgery 86:218–226 (1979).

Nastelin, J. G., "Pancreatic Islet Cell Transplantation: Optimization of Islet Cell Adhesion by Altering Polymer Surface Characteristics," Harvard–M.I.T. Division of Health Sciences and Technology (Feb. 1990).

Naughton, B. et al., "Granulopoiesis and Colony Stimulating Factor Production in Regenerating Liver," Exp. Hematol., 10(5):451–458 (May, 1982).

Naughton, B., et al., "Long–Term Growth of Rat Bone Marrow Cells in a Three–Dimensional Matrix," Medical Laboratory Sciences Department, Hunter College School of Health Sciences, New York, The Anatomical Record, 21 8(1):97a (May, 1987).

Naughton, G., et al., "Erythropoietin Production by Macrophages in the Regenerating Liver," Journal of Surgical Oncology 30:184–197 (1985).

Notter, M. F., et al, "Neuronal Properties of Monkey Adrenal Medulla in vitro," Cell Tissue Res., 244(1):69–76 (1986).

Nyilas, E., et al, "Peripheral Nerve Repair with Bioresorbable Prosthese," Trans. Am. Soc. Artif. Intern. Organs, 29:307–313 (1983).

O'C. Hamilton, Joan, "Miracle Cures May be in Your Cells," BusinessWeek (Dec. 6, 1993).

O'Connor, N., et al., "Grafting of Burns with Cultured Epithelium Prepared from Autologous Epidermal Cells," The Lancet, I(8210):75–78 (Jan., 1981).

O'Donnell & Purl, "Treatment of Vesicoureteric Reflux by Endoscopic Injection of Teflon," British Medical Journal 289:7–9 (Jul. 7, 1984).

Oellrich, R. G., et al. "Biliary Atresia," Neonatal Network pp. 25–30 (Apr., 1987).

Oliwenstein, L., "The Power of Plastics," Discover p. 18 (Dec., 1989).

Omery, Anna, "A Nursing Perspective of the Ethical Issues Surrounding Liver Transplantation," Heart & Lung 17(6):626–630 (Nov., 1988).

Pasik, P., Annals of the N.Y. Academy of Science, 495:674–675 (1987).

Patterson & Gage, "Adrenal Chromaffin Cell–Derived Cholinergic Neurons for Brain Transplants," Caltech Biology pp. 201–202 (1987).

Perlow, M. J., "Brain Grafting as a Treatment for Parkinson's Disease," Neurosurgery 20(2):335–342 (1987).

Pimpl, et al., "Experimentelle Studie zur Frage der Transplantakonditionierung und Transplantatgrofe bei heterotoper autologer Milztransplantation," Lagenbecks Archiv 37215–36218 (Salzburg 1984).

Pimpl, et al., "Perfusion of Autologus Splenic Grafts in Correlation with Specific Immunological Functions An Experimental Study in Pigs," Eur. Surg. Res. 19:53–61 (1987).

Pitman, M. I., et al., "The Use of Adhesives in Chondrocyte Transplantation Surgery: In–Vivo Studies," Bulletin of the Hospital for Joint Diseases Orthopaedic Institute 49(2)213–220 (1989).

Ptasinska–Urbanska, et al, "Intrascleral Introduction of Isolated Allogeneic Chondrocytes Capable of Cartilage Reformation in Rabbitts; Possible Procedure in Treatment of Detachment of the Retina," Exp. Eve. Res., 24(3):241–247 (1977).

Puelacher, W. C., et al., "Tissue–Engineered Growth of Cartilage: the Effect of Varying the Concentration of Chondrocytes Seeded onto Synthetic Polymer Matrices," Int. J. Oral Maxillofac. Sug., 23:49–53 (1994).

Rames & Aaronson, "Migration of Polytef Paste to the Lung and Brain Following Intravesical Injection for the Correction of Reflux," Pediatric Surgery 6(1):239–240 (Jan., 1991).

Redmond, D. E., Jr. et al., "Fetal Neuronal Grafts in Monkeys Give Methyphenyltetrahydropyridine," The Lancet, pp. 1125–1127 (May 17, 1986).

Redmond, D. E. Jr., et al., "Transplants of Primate Neurons," The Lancet,2(8510):1046 (Nov. 1, 1986).

Reid, L. M., et al., "Long–Term Cultures of Normal Rat Hepatocytes on Liver Biomatrix," Ann. NY Acad. Sci. 349:70–76 (1980).

Retik, A. B., et al., "Management of Severe Hypospadias with a 2–Stage Repair," Microbiology & Immunology 152:749–751 (Aug., 1984).

Rhine, W. D., et al., "Polymers for Sustained Macromolecule Release: Procedures to Fabricate Reproducible Delivery Systems and Control Release Kinetics," Journal or Pharmaceutical Sciences, 69(3):265–264 (Mar., 1980).

Rosen, H. B., "Bioerodible Polymers for Controlled Release Systems," Controlled Release Systems: Fabrication Technology, II:83–110.

Rosen, H. B., "Bioerodible Polyanhydrides for Controlled Drug Delivery," 1983 Butterworth & Co. (Publishers) Ltd.

Sapozhnikova, M. A., et al., "Morphological Changes in Splenic Autografts Following Splenectomy: Experimental and Clinical findings," Biological Abstracts, 86(76896) (1987).

Sasaki, K., "Neovascularization in the Splenic Autograft Transplanted into Rat Omentum as Studied by Scanning Electron Microscopy of Vascular Casts," Virchows Arch., 409:325–334 (1986).

Sawada, N., et al., "Effects of Extracellular Matrix Components on the Growth and Differentiation of Cultured Rat Hepatocytes," In Vitro Cellular & Development Biology, 23(4): 267–273 (Apr., 1987).

Schmeck, H. M., Jr., "Doctors try to Capitalize on the Liver's Ability to Regenerate Itself," The New York Times Medical Science, (May 16, 1989).

Schubert & Baird, "Multiple Influences of a Heparin–Binding Growth Factor for Neuronal Development," The Journal of Cell Biology, 104:635–643 (Mar. 1987).

Seckle, "Nerve Regeneration Through Synthetic Biodegradable Nerve Guides: Regulation by the Target Organ," Plast. Reconstr. Surg., 74(2):173–81 (Aug., 1974).

Selden, C., et al., "The Pulmonary Vascular Bed as a Site for Implantation of Isolated Liver Cells in Inbred Rats," Transplantation, 38(1):81–83 (Jul., 1984).

Shine, H. D., et al., "Cultured Peripheral Nervous System Cells Support Peripheral Nerve Regeneration Through Tubes in the Absence of Distal Nerve Stump," Journal of Neuroscience Research, 14:393–401 (1985).

Siegel & Langer, "Controlled Release of Polypeptides and Other Macromolecules," Pharmaceutical Research, pp. 2–10 (1984).

Sirica, A., et al., "Fetal Phenotypic Expression by Adult Rat Hepatocytes on Collagen Gel/Nylon Meshes," Proc. Natl. Acad. Sci. USA, 76(1):283–287 (Jan., 1979).

Sirica, A., et al, "Use of Primary Cultures of Adult Rat Hepatocytes on Collagen Gel–Nylon Mesh to Evaluate Carcinogen–Induced Unscheduled DNA Synthesis," Cancer Research, 40:3259–3267 (Sep. 1980).

Sladek, J. R., Jr., et al, "Reversal of Parkinsonism by Fetal Nerve Cell Transplants in Primate Brain," Annals of the New York Academy of Sciences, 495:641–657 (1987).

Sladek, J. R., Jr., et al., "Survival and Growth of Fetal Catecholamine Neurons Transplanted Into Primate Brain," Brain Research Bulletin, 17:809–818 (1986).

Sladek & Shoulson, "Neural Transplantation: A Call for Patience Rather Than Patients," Science, 386–388 (Jun. 10, 1988).

Sladek, J. R., "Transplantation of Fetal Dopamine Neurons in Primate Brain Reverses MPTP Induced Parkinsonism," Progress in Brain Research,71:309–323 (1987).

Sommer, B. G., et al., "Hepatocellular Transplantation for Treatment of D–Galactosamine–Induced Acute Liver Failure in Rats," Transplant. Proc., 11 (1):578–584 (Mar., 1979).

Stemple, Derek L. Altech Biology (1987).

Strom, S. C., et al., "Isolation, Culture, and Transplantation of Human Hepatocytes," JNCL, 68(5):771–778 (May 1982).

Sudhakaran, P. R., et al., "Modulation of Protein Synthesis and Secretion by Substratum in Primary Cultures of Rat Hepatocytes," Exper. Cell Res. 167:505–516 (1986).

Sullivan, Walter, "Spinal Injury Research Yields a Glimmer of Hope," The New York Times p. C6 (Jul. 14, 1987).

Sutherland, D. E., et al., "Hepatocellular Transplantation in Acute Liver Failure," Surgery 82(1):124–132 (Jul. 1977).

Tachibana, Masaaki, "Ureteral Replacement Using Collagen Sponge Tube Grafts," The Journal of Urologly 133(4):866–869 (Apr., 1985).

Tavassoli, M., et al., "Studies on Regeneration of Heterotopic Splenic Autotransplants," Blood. 41(5):701–709 (May, 1973).

Thompson, J. A., "Heparin–Binding Growth Factor 1 Induces the Formation of Organoid Neovascular Structures in Vivo," Proc. Natl. Acad. Sci USA, 86:7928–27932 (Oct. 1989).

Thompson, J. A., "Implantable Bioreactors: Modern Concepts of Gene Therapy," Current Communications in Molecular Biology, Daniel Marshak, et al., editors, pp. 143–147 (Cold Spring Harbor Laboratory, 1989).

Thuroff, J., et al., "Cultured Rabbit Vesical Smooth Muscle Cells for Lining of Dissolvable Synthetic Prosthesis," Urology 21 (2):155–158 (1983).

Tomomura, A., et al, "The Control of DNA Synthesis in Primary Cultures of Hepatocytes From Adult and Young Rats: Interactions of Extracellular Matrix Components Epidermal Growth Factor, and the Cell Cycle," ©1987 Alan R. Liss, Inc.

Unipoint Industries, Inc., "Polyvinyl Alcohol Foam for Surgical And Industrial Use," Product Review.

UNOS Update, "National Cooperative Transplantation Study Completed," 7(10) (Oct./Nov. 1991).

Upton, J., et al., "Neocartilage Derived from Transplanted Perichondrium: What is it?" Plastic and Reconstructive Surgery 68(2): 166–174 (1981).

Vacanti, J. P. "Beyond Transplantation," Arch. Surgery 123:545–549 (May 1988).

Vacanti, J. P. et al., "Engineered Bone from Polyglycolic Acid Polymer Scaffold and Periosteum," (abstract) Materials Research Society, (Apr. 17–21, 1985).

Vacanti, C. A., et al., "Formation of New Cartilage in Vivo by Implantation of Cell–Polymer Constructs Created in Vitro".

Van der Kwast, T. H., et al., "Establishment and Characterization of Long–Term Primary Mouse Urothelial Cell Cultures," Urological Research, 17(1):290–293 (1989).

Vargo, Rita L., "Infection as a Complication of Liver Transplant," Critical Care Nurse 9(4):52–62.

Vijg, J., et al., "UV–Induced DNA Excision Repair in Rat Fibroblasts During Immortalization and Terminal Differentiation in Vitro," Exp. Cell. Res. 167:517–530 (1986).

Vorstman, Bert, et al., "Polytetrafluoroethylene Injection for Urinary Incontinence in Children," The Journal of Urology 133(2):248–250 (Feb., 1985).

Vroemen, J. P., et al., "Hepatocyte Transplantation for Enzyme Deficiency Disease in Congenic Rats," Transplantation, 42(2):130–135 (1986).

Walker, R. D., et al., "Injectable Bioglass as a Potential Substitute for Injectable Polytetrafluoroethylene," The Journal of Urology 148(1):645–647.

Whitaker, Robert, "Scientists Growing Tissue From 'Seed'," The Boston Globe (Monday, Feb. 22, 1993).

Wozney, J. M., et al., "Novel Regulators of Bone Formation: Molecular Clones and Activities," Science, 242:1528–1534 (Dec. 16, 1988).

Yannas & Burke, "Design of an Artificial Skin. I. Basic Design Principles," Journal of Biomedical Materials Research 14:65–81 (1980).

Yannas, I. V., et al., "Regeneration of Sciatic Nerve Across 15 mm Gap by Use of a Polymeric Template," Polym. Sci. Technol. Iss. Adv. Biomed. Polymer 35:109 (1987).

Yannas and Orgill, "Artifical Skin: A Fifth Route to Organ Repair and Replacement," Iss. Polym. Biomaterial, 106:221–230 (1986).

Yannas and Orgill, "Polymeric Template Facilitates Regeneration of Sciatic Nerve Across 15 MM Gap," Polymer. Material Sci. Eng. 53:216–218 (1985).

Yannas, I. V., et al., "Suppression of in Vivo Degradability and of Immunogenicity of Collagen by Reaction with Glycosaminoglycans," Polymer. Prepar. Am. Chem. Soc. Div. Polym. Chem., 16(2):209–214 (1975).

Yannas, I. V., "Wound Tissue Can Utilize a Polymeric Template to Synthesize a Functional Extension of Skin," Science 215:174–176 (1982).

Yannas, I. V., "What Criteria Should be Used for Designing Artifical Skin Replacement and How Well do the Current Grafting Materials Meet These Criteria?" J. of Trauma, 24(9):S29–S39 (1984).

Report of the International Reflux Study Committee "Medical Versus Surgical Treatment of Primary Vesicoureteral Reflux: A Prospective International Reflux Study in Children," *The Journal of Urology* 125:277–293 (Mar., 1981).

Allcock, at al., "Synthesis of Poly{(amino acid alkylester)phosphazenes}," *Macromolecule* 10:824–830 (1977).

Allcock, H.R., et al., "Phosphonitrilic Compounds. XV.[1] High Molecular Weight Poly{bis(amino)phosphazenes} and Mixed–Substituent Poly(aminophosphazenes)[2]," *Inorg. Chem.* 11:2584–2590 (1972).

Allcock, et al., "Synthesis of Sugar–Substituted Cyclic and Polymeric Phosphazenes and Their Oxidation, Reduction, and Acetylation Reactions," *Macromolecules* 16:715–719 (1983).

Allcock, et al., "Polyphosphazenes with Etheric Side Groups: Prospective Biomedical and Solid Electrolyte Polymers," *Macromolecules* 19:1508–1512 (1986).

Allcock, et al., "Amphiphilic polyposphazenes as membrane materials: influence of side group on radiation cross–linking," *Biomaterials* 19:469–508 (1988).

Allcock, et al., "Glyceryl Polyphosphazenes: Synthesis, Properties, and Hydrolysis," *Macromolecules* 21:1980–1985 (1988).

Allcock, et al., "Hydrolysis Pathways for Aminophosphazenes," *Inorg. Chem.* 21(1):515–521 (1982).

Allcock, et al., "An Ionically Cross–Linkable Polyphosphazene: Poly{bis(carboxylatophenoxy)phosphazene} and Its Hydrogels and Membranes[1]," *Macromolecules* 22:75–79 (1989).

Bennet and Hirt, *J. Dermato. Surg. Oncol.* 19:1066–1073 (1993)*.

Cohen, *J. Dermatol. Surg. Oncol.* 19:614–615 (1993)*.

Cyanamid, "Research Develops Worlds's First Synthetic Absorbable Suture," *Chemistry and Industry*, 905 (1970)*.

E. Goethals, editor, *Concise Encyclopedia of Polymer Science and Polymeric Amines and Ammonium Salts*, (Pergamen Press, Elmsford, NY 1980)*.

Grolleman, et al., "Studies on a Bioerodible Drug Carrier System Based on Polyphosphazene," *J. Controlled Release* 3:143–154 (9186).

Hammond, et al., *Plastic and Reconstructive Surgery*, 92(2):255–259 (1993)*.

Kenna, et al., *Annals of Plastic Surgery* 32:346–349 (1994)*.

Walton and Brown, *Annals of Plastic Surgery* 30(2):105–110 (1993)*.

FLUID WITHDRAWN TO CREATE A SPACE FOR CELL POLYMER INJECTION

FIG. 3c

NEW TISSUE FORMED IN SPACE

BREAST TISSUE ENGINEERING

BACKGROUND OF THE INVENTION

This invention is generally in the field of reconstruction and augmentation of breast tissue.

The breasts, or mammary glands, are modified sweat glands that are attached to the underlying muscle of the anterior chest wall by a layer of connective tissue. Internally, each mammary gland consists of 15-25 lobes, separated by dense connective tissue formed primarily by fibroblasts and bundles of collagen fibers, and adipose tissue containing adipose (fat) cells held together by reticular and collagen fibers. Within each lobe is a lactiferous duct that branches extensively. At the ends of the smallest branches are the glandular epithelial cells (alveolar cells) that synthesize and secrete milk into the duct system. The ducts, which are composed of simple cuboidal and columnar epithelium, and the alveolar cells are embedded in loose connective tissue containing collagen fibers and fibroblasts, lymphocytes, and plasma cells that secrete immunoglobulin A into the milk, conferring passive immunity on the newborn. Just external to the alveolar and duct epithelial cells are myoepithelial cells that respond to neural and hormonal stimuli by contracting and expressing the milk. Each lactiferous duct opens onto the surface of the breast through the skin covering the nipple.

Surgery of the breast can be broadly categorized as cosmetic and therapeutic. Cosmetic surgeries include augmentation, for example, using implants; reduction; and reconstruction. Therapeutic surgery, which is the primary treatment for most early cancers, includes radical surgery that may involve removal of the entire soft tissue anterior chest wall and lymph nodes and vessels extending into the head and neck; lumpectomy, which may involve only a small portion of the breast; and laser surgery for destruction of small regions of tissue. Reconstructive surgery and the use of implants is frequently combined with radical breast surgery. The radical mastectomy involves removal of the breast, both the major and minor pectoralis muscles, and lymph nodes.

More than 250,000 reconstructive procedures are performed on the breast each year. Women afflicted with breast cancer, congenital defects or damage resulting from trauma have very few alternatives to reconstruction. Breast reconstruction is frequently used at the time or, or shortly after, mastectomy for cancer. Reconstructive procedures frequently involve moving vascularized skin flaps with underlying connective and adipose tissue from one region of the body, e.g., the buttocks or the abdominal region, to the breast region. Surgeons also use breast implants for reconstruction.

There are numerous surgical methods of breast reconstruction, including tissue expansion followed by silicone implantation, latissimus dorsi flap, pedicled transversus abdominis myocutaneous flap (TRAM), free TRAM flap, and free gluteal flap. Full reconstruction often requires numerous procedures in addition to the mastectomy and primary reconstruction. Procedures include tissue-expander exchange for permanent implant, nipple reconstruction, revision of reconstruction, and mastopexy/reduction.

Unfortunately, silicone prosthesis, which are used for reconstruction and augmentation, have caused numerous medical complications. It would be desirable to have an alternative material for implantation.

Even with reconstructive surgical methods that are currently in use, it is extremely difficult to achieve tissue that looks and feels normal, particularly when there has been extensive removal of associated muscle tissue.

It is therefore an object of the present invention to provide methods and compositions for reconstruction and augmentation of breast tissue.

It is a further object of the present invention to provide methods and materials to provide breast structure which is tissue, not foreign material such as silicone, and has the appearance of normal tissue.

SUMMARY OF THE INVENTION

Methods and compositions are described herein for reconstruction or augmentation of breast tissue. Dissociated cells, preferably muscle cells, are implanted in combination with a suitable biodegradable, polymeric matrix to form new tissue. There are two forms of matrices which can be used: a polymeric hydrogel formed of a material such as alginate having cells suspended therein, and a fibrous matrix having an interstitial spacing between about 100 and 300 microns. Preferred polymeric materials are those degrading over about one to two months, such as polylactic acid-glycolic acid copolymers. The matrices can be seeded prior to implantation or implanted, allowed to vascularize, then seeded with cells. In a preferred embodiment, the cell-matrix structures are implanted in combination with tissue expander devices. As cell-matrix is implanted, or cells proliferate and form new tissue, the expander size is decreased, until it can be removed and the desired reconstruction or augmentation is obtained. The preferred cell types are muscle cells, although other types of mesenchymal cells, fibroblasts, chondrocytes, and adipocytes can be used. Cells obtained from tissue such as the labia can be used for specialized applications such as formation of a nipple type tissue. Other materials, such as bioactive molecules that enhance vascularization of the implanted tissue and/or which inhibit ingrowth of fibrotic tissue, can be implanted with the matrix to enhance development of more normal tissue.

The cell-matrix structures can be implanted at the time of surgery to remove cancerous breast tissue, during subsequent reconstructive surgery, or over a period of time, for example, weekly, if serial injections of cell-hydrogel suspensions are used to create the new tissue.

BRIEF DESCRIPTION OF THE DRAWINGS

FIG. 3A is the tissue expander maximally expanded; FIG. 3B is with fluid withdrawn from the expander to create a space between the abutting tissue and the expander, into which cell-polymer suspension is injected; and FIG. 3C is with the expander maximally deflated, with new tissue forming in the space occupied by much of the tissue expander expanded as in FIG. 1.

DETAILED DESCRIPTION OF THE INVENTION

I. Cells to be Implanted

Cells to be implanted are dissociated using standard techniques such as digestion with a collagenase, trypsin or other protease solution. Preferred cell types are mesenchymal cells, especially smooth or skeletal muscle cells, myocytes (muscle stem cells), chondrocytes, adipocytes, fibromyoblasts, and ectodermal cells, including ductile and skin cells. In some cases it may also be desirable to include nerve cells. Cells can be normal or genetically engineered to provide additional or normal function.

Cells are preferably autologous cells, obtained by biopsy and expanded in culture, although cells from close relatives or other donors of the same species may be used with appropriate immunosuppression. Immunologically inert cells, such as embryonic cells, stem cells, and cells genetically engineered to avoid the need for immunosuppression can also be used. Methods and drugs for immunosuppression are known to those skilled in the art of transplantation. A preferred compound is cyclosporin using the recommended dosages.

In the preferred embodiment, skeletal or smooth muscle cells are obtained by biopsy and expanded in culture for subsequent implantation. Skeletal or smooth can be easily obtained through a biopsy anywhere in the body, for example, skeletal muscle biopsies can be obtained easily from the arm, forearm, or lower extremities, and smooth muscle can be obtained from the area adjacent to the subcutaneous tissue throughout the body. To obtain either type of muscle, the area to be biopsied can be locally anesthetized with a small amount of lidocaine injected subcutaneously. Alternatively, a small patch of lidocaine jelly can be applied over the area to be biopsied and left in place for a period of 5 to 20 minutes, prior to obtaining biopsy specimen. The biopsy can be effortlessly obtained with the use of a biopsy needle, a rapid action needle which makes the procedure extremely simple and almost painless. With the addition of the anesthetic agent, the procedure would be entirely painless. This small biopsy core of either skeletal or smooth muscle can then be transferred to media consisting of phosphate buffered saline. The biopsy specimen is then transferred to the lab where the muscle can be grown utilizing the explant technique, wherein the muscle is divided into very pieces which are adhered to culture plate, and serum containing media is added. Alternatively, the muscle biopsy can be enzymatically digested with agents such as trypsin and the cells dispersed in a culture plate with any of the routinely used medias. After cell expansion within the culture plate, the cells can be easily passaged utilizing the usual technique until an adequate number of cells is achieved.

II. Device Fabrication

Three principle types of matrices can be used to create new tissues or augment tissues. The term "bioerodible", or "biodegradable", as used herein refers to materials which are enzymatically or chemically degraded in vivo into simpler chemical species.

Hydrogel Polymer Solutions

In one embodiment, polymers that can form ionic hydrogels which are malleable are used to support the cells. Injecting a suspension of cells in a polymer solution may be performed to improve the reproducibility of cell seeding throughout a device, to protect the cells from shear forces or pressure induced necrosis, or to aid in defining the spatial location of cell delivery. The injectable polymer may also be utilized to deliver cells and promote the formation of new tissue without the use of any other matrix.

In a preferred embodiment, the hydrogel is produced by cross-linking the ionic salt of a polymer with ions, whose strength increases with either increasing concentrations of ions or polymer. The polymer solution is mixed with the cells to be implanted to form a suspension, which is then injected directly into a patient prior to hardening of the suspension. The suspension subsequently hardens over a short period of time due to the presence in vivo of physiological concentrations of ions such as calcium in the case where the polymer is a polysaccharide such as alginate.

Polymers

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure:

where n is an integer.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is cross-linked with dissolved multivalent cations in aqueous media at room temperature or below to form hydrogel matrices.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegradable, as used herein, means a polymer that dissolves or degrades within a period that is acceptable in the desired application (usually in vivo therapy), less than about five years and most preferably less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., Macromolecule 10:824–830 (1977).

Methods for synthesis and the analysis of various types of polyphosphazenes are described by Allcock, H. R.; et al., Inorg. Chem. 11, 2584(1972); Allcock, et al., Macromolecules 16, 715(1983); Allcock, et al., Macromolecules 19, 1508(1986); Allcock, et al., Biomaterials, 19, 500(1988); Allcock, et al., Macromolecules 21, 1980(1988); Allcock, et al., Inorg. Chem. 21(2), 515–521(1982); Allcock, et al., Macromolecules 22, 75(1989); U.S. Pat. Nos. 4,440,921, 4,495,174 and 4,880,622 to Allcock, et al.; U.S. Pat. No. 4,946,938 to Magill, et al.; and Grolleman, et al., J. Controlled Release 3, 143(1986), the teachings of which are specifically incorporated herein by reference.

Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, NY 1980). Many polymers, such as poly(acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3 N^+-\text{VVV}-^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine), examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3 H$ groups such as sulfonated polystyrene, and polystyrene with carboxylic acid groups.

Method for Making Cell Suspensions

The polymer is dissolved in an aqueous solution, preferably a 0.1 M potassium phosphate solution, at physiological pH, to a concentration forming a polymeric hydrogel, for example, for alginate, of between 0.5 to 2% by weight, preferably 1%, alginate. The isolated cells are suspended in the polymer solution to a concentration of between 1 and 50 million cells/ml, most preferably between 10 and 20 million cells/ml.

Polymeric Matrix

Matrix Configuration

For an organ to be constructed, successfully implanted, and function, the matrices must have sufficient surface area and exposure to nutrients such that cellular growth and differentiation can occur prior to the ingrowth of blood vessels following implantation. The time required for successful implantation and growth of the cells within the matrix is greatly reduced if the area into which the matrix is implanted is prevascularized. After implantation, the configuration must allow for diffusion of nutrients and waste products and for continued blood vessel ingrowth as cell proliferation occurs.

The organization of the tissue may be regulated by the microstructure of the matrix. Specific pore sizes and structures may be utilized to control the pattern and extent of fibrovascular tissue ingrowth from the host, as well as the organization of the implanted cells. The surface geometry and chemistry of the matrix may be regulated to control the adhesion, organization, and function of implanted cells or host cells.

In the preferred embodiment, the matrix is formed of polymers having a fibrous structure which has sufficient interstitial spacing to allow for free diffusion of nutrients and gases to cells attached to the matrix surface. This spacing is typically in the range of 100 to 300 microns, although closer spacings can be used if the matrix is implanted, blood vessels allowed to infiltrate the matrix, then the cells are seeded into the matrix. As used herein, "fibrous" includes one or more fibers that is entwined with itself, multiple fibers in a woven or non-woven mesh, and sponge like devices.

Cells can either be implanted after seeding onto a matrix or injected into a matrix already implanted at the desired site. The latter has the advantage that the matrix can be used to prevascularize the site. In this case, the design and construction of the scaffolding is of primary importance. The matrix should be a pliable, non-toxic, injectable porous template for vascular ingrowth. The pores should allow vascular ingrowth and the injection of cells such as muscle cells without damage to the cells or patient. These are generally interconnected pores in the range of between approximately 100 and 300 microns. The matrix should be shaped to maximize surface area, to allow adequate diffusion of nutrients and growth factors to the cells and to allow the ingrowth of new blood vessels and connective tissue. At the present time, a porous structure that is resistant to compression is preferred for implantation, prevascularization, followed by seeding.

In the embodiment where the matrix is prevascularized, it may be desirable to incorporate into the matrix means for dispersing the cells throughout the matrix, for example, using catheters which can be removed following seeding.

The overall, or external, matrix configuration is dependent on the tissue which is to be reconstructed or augmented. In most cases, the cell-matrix structure will be similar to the silicone implants now used, which are essentially disks that deform due to gravity to form a teardrop shape. The shape can also be obtained using struts, as described below, to impart resistance to mechanical forces and thereby yield the desired shape. The shape of the matrix per se will not be disk shaped, but will appear disk shaped when seeded with the cells to be implanted, or will create the outline of a disk or tear drop shape following implantation.

Polymers

Either natural or synthetic polymers can be used to form the matrix, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, teflon®, and nylon. Although non-degradable materials can be used to form the matrix or a portion of the matrix, they are not preferred. The preferred non-degradable material for implantation of a matrix which is prevascularized prior to implantation of dissociated cells is a polyvinyl alcohol sponge, or alkylation, and acylation derivatives thereof, including esters. A non-absorbable polyvinyl alcohol sponge is available commercially as Ivalon™, from Unipoint Industries. Methods for making this material are described in U.S. Pat. Nos. 2,609,347 to Wilson; 2,653,917 to Hammon, 2,659,935 to Hammon, 2,664,366 to Wilson, 2,664,367 to Wilson, and 2,846,407 to Wilson, the teachings of which are incorporated by reference herein. These materials are all commercially available.

Examples of natural polymers include proteins such as albumin, collagen, synthetic polyamino acids, and prolamines, and polysaccharides such as alginate, heparin, and other naturally occurring biodegradable polymers of sugar units.

PLA, PGA and PLA/PGA copolymers are particularly useful for forming the biodegradable matrices. PLA polymers are usually prepared from the cyclic esters of lactic acids. Both L(+) and D(-) forms of lactic acid can be used to prepare the PLA polymers, as well as the optically inactive DL-lactic acid mixture of D(-) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. Nos. 1,995,970 to Dorough; 2,703,316 to Schneider; 2,758,987 to Salzberg; 2,951,828 to Zeile; 2,676,945 to Higgins; and 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. A preferred material is poly(lactide-co-glycolide) (50:50), which degrades in about six weeks following implantation (between one and two months).

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

Polymer Coatings

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture. A preferred material for coating the polymeric matrix is polyvinyl alcohol or collagen.

Struts

In some embodiments it may be desirable to create additional structure using devices provided for support, referred to herein as "struts". These can be biodegradable or non-degradable polymers which are inserted to form a more defined shape than is obtained using the cell-matrices, especially the hydrogel-cell suspensions. An analogy can be made to a corset, with the struts acting as "stays" to push the surrounding tissue and skin up and away from the implanted cells. In a preferred embodiment, the struts are implanted prior to or at the time of implantation of the cell-matrix structure. The struts are formed of a polymeric material of the same type as can be used to form the matrix, as listed above, having sufficient strength to resist the necessary mechanical forces.

Tissue Expanders

Alternatively, or in addition, tissue expanders can be used to create additional space for implantation of cell-matrix structures. Tissue expanders are commercially available and routinely used for expansion of skin, for example, prior to plastic surgery, as reviewed by Cohen, J. Dermatol. Surg. Oncol. 19:614–615(1993), Bennett and Hirt, J. Dermatol. Surg. Oncol. 19:1066–1073(1993), Hammond, et al., Plastic and Reconstructive Surgery, 92(2):255–259 (1993), Walton and Brown, Annals of Plastic Surgery 30(2), 105–110 (February 1993), Kenna, et al., Annals of Plastic Surgery 32, 346–349(1994), the teachings of which are incorporated herein. When skin is tensioned for long periods of time, weeks to months, it responds by a very significant stretching. This is associated with metabolic activity and tissue growth. The generally accepted definition of a tissue expander is a device that resides beneath the surface of the skin which is used to stretch the skin. A spherical tissue expander is a multi-dimensional expander, typically applied by volumetrically expanding a subcutaneous space with an inflatable device. Alternatively, multiple bolus materials can be implanted and the device shrunk or replaced through removal of one or more of the bolus materials.

The use of tissue expanders in breast reconstruction are well understood (see, for example, Hammond, et al., 1993). Several different types of anatomically oriented or shaped expanders have been designed to give a more natural contour to the reconstructed breast. Devices are commercially available, for example, from McGhan Medical Corporation, Santa Barbara, Calif., Dow Corning-Wright, Arlington, Tenn., and Mentor Corporation, Goleta, Ga.

It is important to remove pressure from the implanted cells which can kill the cells. For example, in one preferred embodiment described in more detail below, a hydrogel-cell suspension is injected into the area where tissue is to be created. The space for injection of the cell-polymer suspension is created by implantation of a tissue expander prior to injection of the hydrogel-cell suspension. The tissue expander is inflated or expanded through implantation of a desired number of modules, to maximize the space and skin required for formation of tissue. As shown in detail in FIGS. 3A, 3B, and 3C, each time cell-matrix is injected, the tissue expander is deflated or a module is removed to leave a space of an equivalent amount to the volume of cell-matrix injected. Once the space is essentially filled with new tissue or cell-matrix suspension, the tissue expander is removed, using in most cases a local anesthetic and minor incision.

Additives to Polymer Matrices

In some embodiments it may be desirable to add bioactive molecules to the cells. A variety of bioactive molecules can be delivered using the matrices described herein. These are referred to generically herein as "factors" or "bioactive factors".

In the preferred embodiment, the bioactive factors are growth factors, angiogenic factors, compounds selectively inhibiting ingrowth of fibroblast tissue such as antiinflammatories, and compounds selectively inhibiting growth and proliferation of transformed (cancerous) cells. These factors may be utilized to control the growth and function of implanted cells, the ingrowth of blood vessels into the forming tissue, and/or the deposition and organization of fibrous tissue around the implant.

Examples of growth factors include heparin binding growth factor (hbgf), transforming growth factor alpha or beta (TGFβ), alpha fibroblastic growth factor (FGF), epidermal growth factor (TGF), vascular endothelium growth factor (VEGF), some of which are also angiogenic factors. Other factors include hormones such as insulin, glucagon, and estrogen. In some embodiments it may be desirable to incorporate factors such as nerve growth factor (NGF) or muscle morphogenic factor (MMP).

Steroidal antiinflammatories can be used to decrease inflammation to the implanted matrix, thereby decreasing the amount of fibroblast tissue growing into the matrix.

Where selective chemotherapeutic agents are available which do not inhibit growth of normal cells, such as antibody targeted chemotherapeutic agents, these can be incorporated into the matrix and used to inhibit any residual cancer cells remaining following a mastectomy.

These factors are known to those skilled in the art and are available commercially or described in the literature. In vivo dosages are calculated based on in vitro release studies in cell culture; an effective dosage is that dosage which increases cell proliferation or survival as compared with controls, as described in more detail in the following examples. Preferably, the bioactive factors are incorporated to between one and 30% by weight, although the factors can be incorporated to a weight percentage between 0.01 and 95 weight percentage.

Bioactive molecules can be incorporated into the matrix and released over time by diffusion and/or degradation of the matrix, they can be suspended with the cell suspension, they can be incorporated into microspheres which are suspended with the cells or attached to or incorporated within the matrix, or some combination thereof. Microspheres would typically be formed of materials similar to those forming the matrix, selected for their release properties rather than structural properties. Release properties can also be determined by the size and physical characteristics of the microspheres. Suitable microspheres and methods for their use in tissue generation is described in U.S. Ser. No. 08/358,235 by David J. Mooney, Robert S. Langer, and Joseph P. Vacanti, entitled "Localized Delivery of Factors Enhancing Survival of Transplanted Cells", co-filed herewith in the U.S. Patent and Trademark Office on Dec. 16, 1994, the teachings of which are incorporated herein.

III. Methods for Implantation

As discussed generally above, there are three methods which can be used to create new breast tissue. These can be used alone or in various combinations. Variations include where the cells are introduced into the matrix, which can be a hydrogel solution or a solid fibrous matrix, before implantation or serially introduced after matrix implantation to allow pre-vascularization of the matrix. The form of the engineered tissue can be regulated by utilizing a tissue expander to create the desired space for tissue formation, and then serially deflating the tissue expander while the cells of interest are delivered to this newly created space. This allows the tissue form to be pre-defined, and allows serial introduction of cells for forming new tissue. Alternatively, a pre-formed matrix can be implanted, allowed to vascularize, then be seeded with dissociated cells which form new tissue, preferably as the matrix degrades. Selection of the appropriate system depends on the degree of augmentation required, and determines whether the whole injection can be performed at once, or alternatively, performed in a sequential manner, so as to allow for tissue formation with adequate vascularization before subsequent injections are performed.

Selection of cell type can be used to vary the texture of the implanted material, as well as the appearance. For example, cartilage can be used, if a more rigid implant is desired. In some embodiments it may be desirable to create softer tissue, for example, using adipocytes or other soft tissue components.

Figure 1:
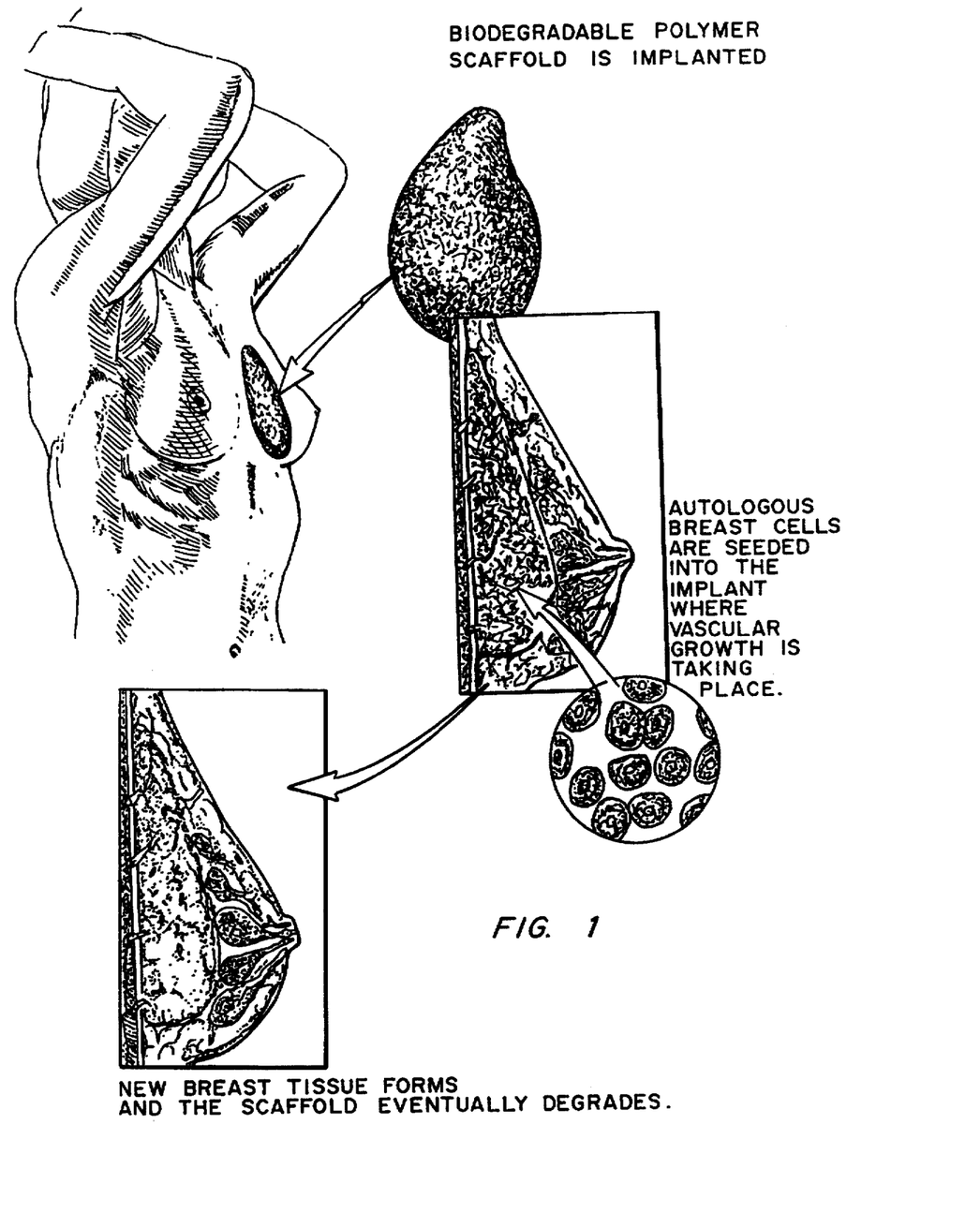
FIG. 1 is a schematic of the process for implantation of dissociated cells on a polymeric matrix into breast for breast tissue augmentation.

FIG. 1 is a schematic of the process for implantation of dissociated cells 10 on a polymeric matrix 12 into breast 14 for breast tissue augmentation. The cells attach to the matrix 12, which is originally disk shaped but deforms to a tear drop shape when implanted. As vascularization occurs and the matrix degrades, new tissue is formed.

Figure 2:
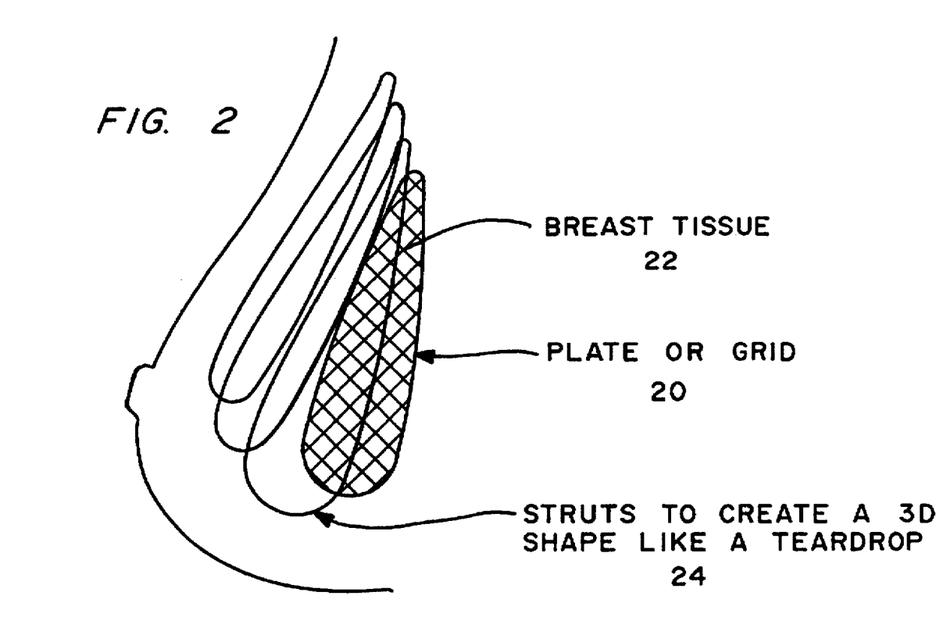
FIG. 2 is a schematic of a fibrous plate implanted into breast tissue with struts to provide support of surrounding tissue and skin and allow new tissue to be formed within the strut following injection of a cell-hydrogel suspension.

FIG. 2 is a schematic of a fibrous plate 20 implanted into breast tissue 22 with struts 24 to provide support of surrounding tissue and skin and allow new tissue to be formed within the strut following injection of a cell-hydrogel suspension (not shown).

Figure 3A:
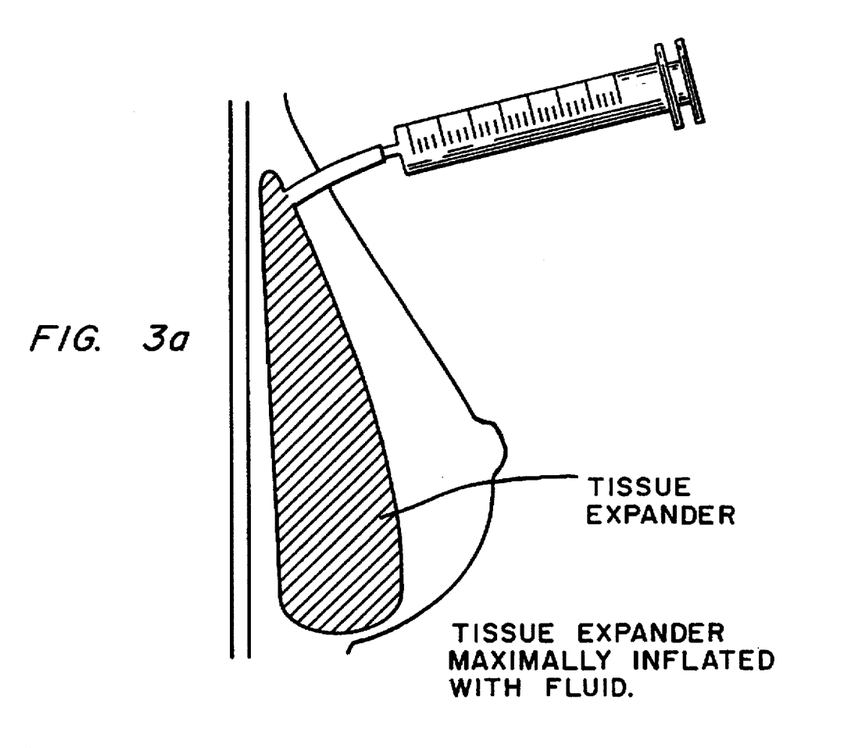
FIGS. 3A, 3B and 3C are schematics of the serial injection of a cell-hydrogel suspension following implantation of a tissue expander, with the tissue expander being decreased in size each time the suspension is injected.
Figure 3B:
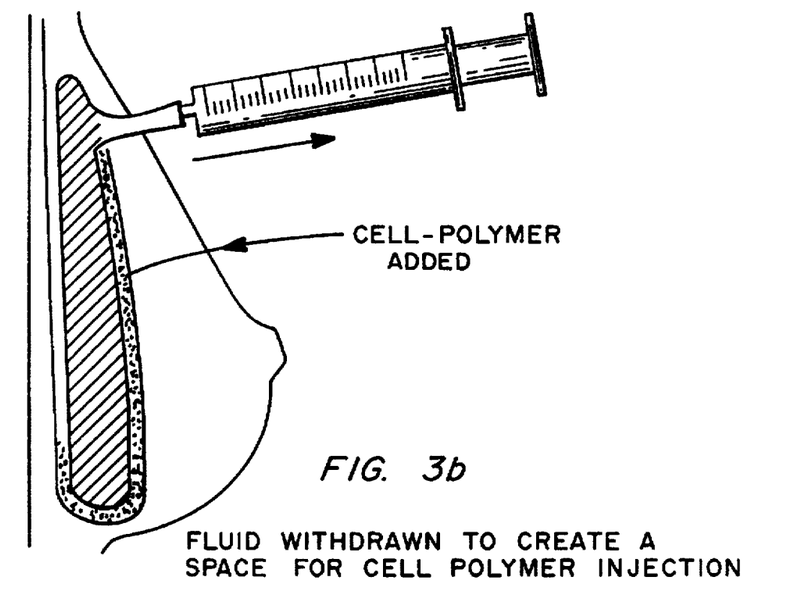
Figure 3C:
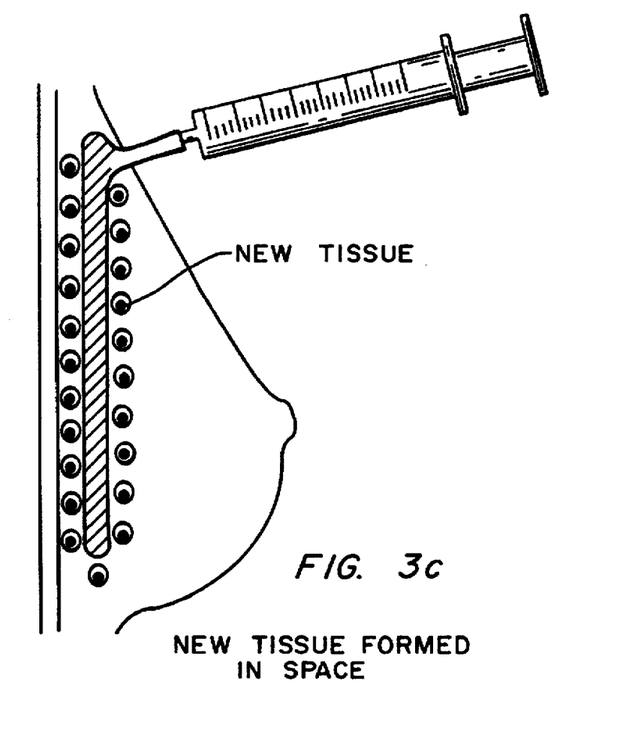

FIGS. 3A, 3B and 3C are schematics of the serial injection of a cell-hydrogel suspension following implantation of a tissue expander (FIG. 3A), with the tissue expander being decreased in size each time the suspension is injected (FIG. 3B), so that new tissue forms in the space left as the expander is decreased in volume (FIG. 3C).

Modifications and variations of the method and compositions described herein will be obvious to those skilled in the art from the foregoing detailed description. Such modifications and variations are intended to come within the scope of the appended claims.

We claim:

1. A method for augmentation or reconstruction of breast tissue comprising implanting into the breast area of a patient in need of treatment thereof an effective amount of dissociated human cells selected from the group consisting of mesenchymal cells, myocytes, chondrocytes, adipocytes, fibromyoblasts, and ectodermal cells, in combination with a polymeric matrix shaped to form breast tissue, wherein the cells proliferate to form or augment tissue with the texture, feel and general appearance similar to that of normal breast.

2. The method of claim 1 wherein the cells are smooth or skeletal muscle cells.

3. The method of claim 1 further comprising implanting the cells at the same time as the matrix.

4. The method of claim 1 wherein the matrix is a biocompatible, biodegradable hydrogel.

5. The method of claim 1 wherein the matrix is implanted, allowed to vascularize, then seeded with cells.

6. The method of claim 1 wherein the matrix is a fibrous, polymeric matrix.

7. The method of claim 1 wherein the matrix is formed of a biodegradable polymer.

8. The method of claim 1 further comprising implanting struts into the patient at the site where the matrix is to be implanted to support the surrounding tissue and prevent the tissue from deforming the matrix.

9. The method of claim 1 further comprising implanting bioactive molecules selected from the group of molecules enhancing vascularization, cell survival, proliferation or differentiation, inhibiting ingrowth of fibrotic tissue, inhibiting growth of cancerous cells, and inhibiting inflammation.

10. The method of claim 1 further comprising implanting a tissue expander into the patient at the site where the matrix and cells are to be implanted, wherein the expander is implanted prior to implanting the cells or matrix.

11. The method of claim 1 further comprising seeding the matrix with nerve cells.

* * * * *